United States Patent [19]
Greenwald et al.

[11] Patent Number: 5,902,588
[45] Date of Patent: May 11, 1999

[54] NON-ANTIGENIC AMINE DERIVED POLYMERS AND POLYMER CONJUGATES

[75] Inventors: Richard B. Greenwald, Somerset; Anthony Martinez, Hamilton Square; Annapurna Pendri, Matawan, all of N.J.

[73] Assignee: Enzon, Inc., Piscataway, N.J.

[21] Appl. No.: 08/974,532

[22] Filed: Nov. 19, 1997

Related U.S. Application Data

[60] Division of application No. 08/465,403, Jun. 5, 1995, Pat. No. 5,730,990, which is a continuation-in-part of application No. 08/265,593, Jun. 24, 1994, abandoned.

[51] Int. Cl.⁶ .......................... A61K 45/00; C08F 110/02
[52] U.S. Cl. .................................. 424/278.1; 424/78.18; 424/279.1; 526/352; 526/436; 526/936; 530/402; 530/815; 546/1; 546/157
[58] Field of Search .............................. 424/279.1, 278.1, 424/78.17, 78.18; 526/352, 436, 936; 546/1, 157; 530/402, 815

[56] References Cited

U.S. PATENT DOCUMENTS

| | | |
|---|---|---|
| 4,101,380 | 7/1978 | Rubinstein et al. . |
| 4,179,337 | 12/1979 | Davis et al. . |
| 4,275,000 | 6/1981 | Ross . |
| 4,481,190 | 11/1984 | Nestor et al. . |
| 4,680,338 | 7/1987 | Sundoro . |
| 4,690,916 | 9/1987 | Nestor, Jr. et al. . |
| 4,904,582 | 2/1990 | Tullis . |
| 5,091,176 | 2/1992 | Braatz et al. . |
| 5,093,531 | 3/1992 | Sano et al. . |
| 5,122,614 | 6/1992 | Zalipsky . |
| 5,162,505 | 11/1992 | Dean et al. . |
| 5,183,660 | 2/1993 | Ikeda et al. . |
| 5,214,131 | 5/1993 | Sano et al. . |
| 5,252,714 | 10/1993 | Harris et al. . |

FOREIGN PATENT DOCUMENTS

| | | |
|---|---|---|
| 0236987 | 9/1987 | European Pat. Off. . |
| 0 369 752 | 5/1990 | European Pat. Off. . |
| 0510356 | 10/1992 | European Pat. Off. . |
| 0539167 | 10/1992 | European Pat. Off. . |
| 0539167 | 4/1993 | European Pat. Off. . |
| 0 593 868 A1 | 4/1994 | European Pat. Off. . |
| 0 632 082 A1 | 1/1995 | European Pat. Off. . |
| 9102763 | 3/1991 | WIPO . |
| WO 94/20453 | 9/1994 | WIPO . |
| WO 95/11924 | 5/1995 | WIPO . |

OTHER PUBLICATIONS

Harris, J. "Laboratory Synthesis of Polyethylene Glycol Derivatives"; *Macromol.Chem Phys.*, C25(3), pp. 325–373 (1985).

Nishimura et al., Enzyme 26, pp. 49–53 (1981).

Kimura et al., Proceeding of the Society for Experimental Biology and Medicine, 188, pp. 364–369 (1988).

Zalipsky et al., Eur. Polym. J., vol. 19., No. 12, pp. 1177–1183, (1983).

Harris, J. M. ed. Poly(ethylene glycol) Chemistry, 1992, pp. 377–381.

Ouchi et al, Drug Design and Discovery, vol. 9, pp. 93–105 (1992).

*Primary Examiner*—Ponnathapura Achutamurthy
*Assistant Examiner*—P. Ponnaluri
*Attorney, Agent, or Firm*—Roberts & Mercanti, LLP

[57] ABSTRACT

Substantially non-antigenic polymers containing pI and/or pH optimum modulating moieties are disclosed. The polymers are useful as intermediates for synthesis of amine-based polymers and in the formation of activated polymers for conjugation with nucleophiles. Conjugates and methods of preparation and treatment with the conjugates are also disclosed.

14 Claims, 4 Drawing Sheets

NON-ANTIGENIC AMINE DERIVED POLYMERS AND POLYMER CONJUGATES

CROSS-REFERENCE TO RELATED APPLICATIONS

This application is a divisional of U.S. Ser. No. 08/465,403, filed Jun. 5, 1995, which is now U.S. Pat. No. 5,730,990, which in turn is a continuation-in-part of U.S. patent application Ser. No. 08/265,593 filed Jun. 24, 1994, now abandoned.

BACKGROUND OF THE INVENTION

1. Field of the Invention

The present invention relates to polymers which are useful in extending the in vivo circulating life of biologically active materials. The invention also relates to conjugates made with the polymers.

2. Description of Prior Art

Some of the initial concepts of coupling peptides or polypeptides to poly(ethylene glycol) PEG and similar water-soluble poly(alkylene oxides) are disclosed in U.S. Pat. No. 4,179,337, the disclosure of which is incorporated herein by reference. Polypeptides modified with these polymers exhibit reduced immunogenicity or antigenicity and circulate in the bloodstream longer than unmodified versions.

To conjugate poly(alkylene oxides), one of the hydroxyl end-groups is converted into a reactive functional group. This process is frequently referred to as "activation" and the product is called an "activated poly(alkylene oxide)". Other substantially non-antigenic polymers are similarly "activated" or functionalized.

The activated polymers are reacted with a therapeutic agent having nucleophilic functional group(s) that serve as attachment site(s). One nucleophilic functional group commonly used as an attachment site is the epsilon-amino group of lysines. Free carboxylic acid groups, suitably activated carbonyl groups, oxidized carbohydrate moieties, hydroxyl and mercapto groups have also been used as attachment sites.

Over the years, one shortcoming observed with polymer conjugation is that the conjugate has a different pI than the unmodified protein, enzyme, etc. For example, pegylation, i.e. attachment of the polymer, of lysine amino groups result in a decrease in the isoelectric point and changes the pH optimum, i.e the pH at which maximum bioactivity is observed. In some cases, it would be beneficial to restore the original pI or even alter the pI value of the polymer conjugate in order to optimize bioactivity at physiologic pH.

The present invention provides solutions to this problem.

SUMMARY OF THE INVENTION

In one aspect of the invention, there are provided amine-based polymer intermediates having the formula:

R—B (I)

wherein (R) is a water-soluble, substantially non-antigenic polymer residue and (B) is preferably a secondary amine or a tertiary amine. Suitable secondary amines are of the formula:

—NH(CH$_2$)$_n$X (II)

wherein:

(n) is an integer from 1–12, inclusive; and

X is selected from the group consisting of H; OH; CO$_2$R$_1$, where R$_1$ is H or a C$_{1-6}$ alkyl; halogen, aryl moieties and heteroaromatic moieties.

Suitable tertiary amines can be selected from:

  (III)

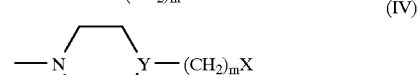  (IV)

  (V)

  (VI)

wherein (m) is an integer from 0–12, inclusive;

(X) is selected from the group consisting of H, OH, CO$_2$R$_1$, where R$_1$ is H or a C$_{1-6}$ alkyl, halogen, aryl moieties and heteroaromatic moieties;

(Y) is N or CH; and (Z) is a C$_{1-6}$ alkyl.

The polymer is preferably a poly(alkylene oxide) residue such as a poly(ethylene glycol) having a molecular weight between about 200 and about 100,000. In addition, the polymer is preferably capped with a C$_{1-4}$ alkyl group on the end opposite (i.e. distal to) the B moiety.

In another aspect of the invention, there are provided substantially non-antigenic polymers of the formula:

R—B'—W—L (VII)

wherein (R) is as defined above; (B') is NY, where Y is H, i.e. a secondary amine or a C$_{1-6}$ alkyl or cycloalky, i.e. a tertiary amine. (W) is a spacer group, such as a C$_{1-6}$ alkyl and (L) is a functional group capable of bonding with nucleophiles.

Other aspects of the invention include polymer conjugates containing biologically-active materials, described as nucleophiles herein as well as methods of conjugate preparation. In these aspects of the invention, the conjugates are of the formula:

[R—B'—W—L']$_z$—(nucleophile)

wherein:

(R), (B') and (W) are as described above;

(L$^1$) represents a covalent linkage between (R—B'—W) and a nucleophile; and (z) represents the number of polymers attached to the nucleophile.

The biologically active materials include proteins, peptides, enzymes, medicinal chemicals or organic moieties whether synthesized or isolated from nature. The conjugation methods include contacting a nucleophile, i.e. a biologically active material, capable of undergoing a substitution reaction with a polymer described. The reaction is carried out under conditions sufficient to effect attachment while maintaining at least a portion of the biological activity.

The present invention also includes methods of treating various maladies and conditions. In this aspect, a mammal in need of treatment is administered an effective amount of a conjugate containing a biologically-active material such as a protein, enzyme or organic moiety attached to a polymer of the present invention.

Some of the chief advantages of the present invention are that the amine-derived polymers impart a pI and/or pH modulating effect to the conjugate. Thus, the isoelectric point of bio-active materials included in the conjugate can be adjusted to a desired point. This is to be contrasted with the effect observed with conventional activated polymers where shifts in isoelectric points can be observed, often to the detriment of optimal activity.

In addition, in those aspects of the invention where anionic groups are included as part of the amine-bearing moiety, the in vivo circulating life of the conjugates is further prolonged due to reduced renal filtration.

DETAILED DESCRIPTION OF THE INVENTION

1. POLYMER RESIDUES

Figure 1:
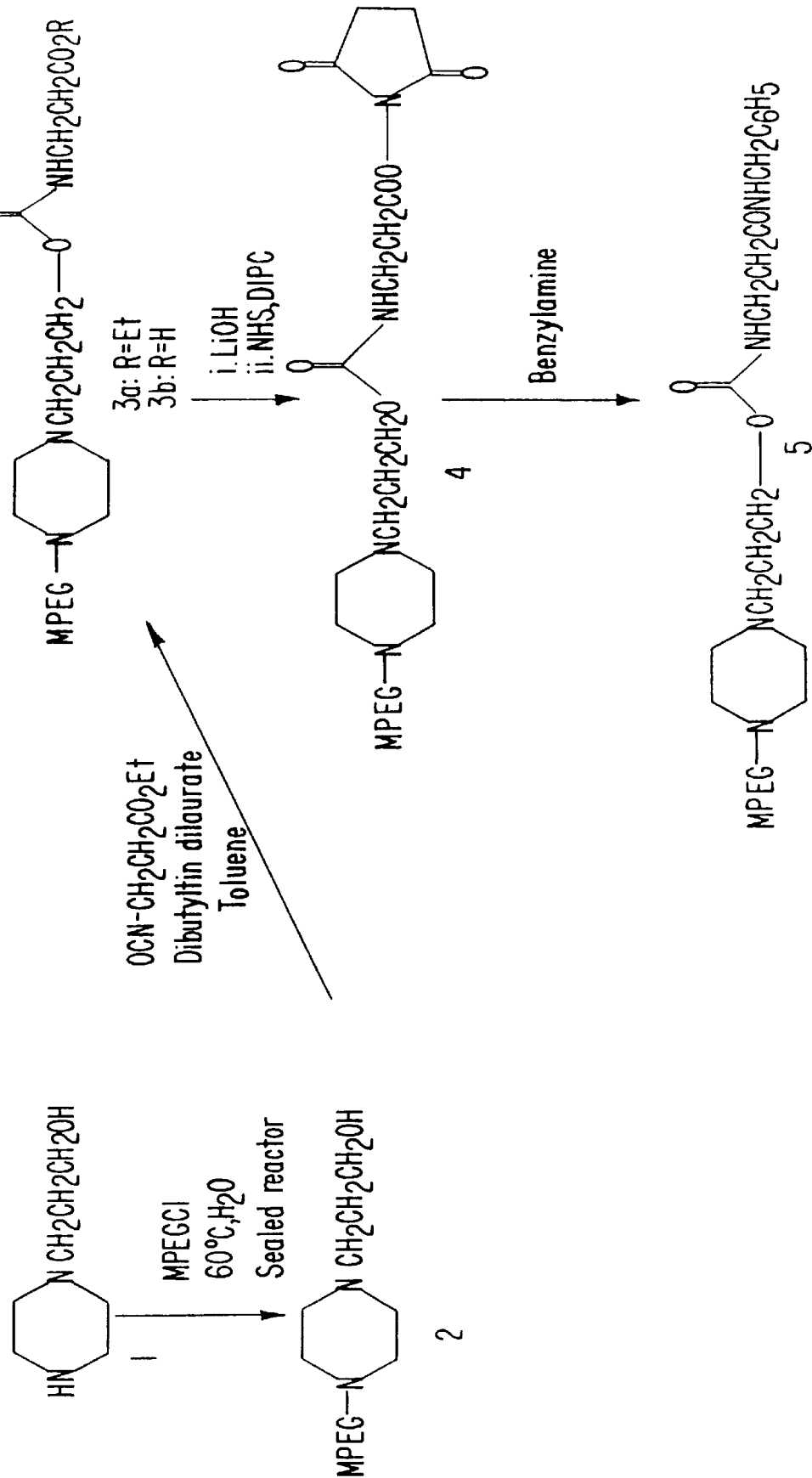
FIG. 1 is a schematic representation of synthesis techniques carried out in accordance with the invention to prepare formula (I) R—B polymer intermediates and the compounds of Examples 1 and 3–6.

The activated polymers of the present invention are preferably prepared from poly(alkylene oxides) (PAO's) that are water soluble at room temperatures. Within this group are mono-substituted polyalkylene oxide derivatives such as methoxypoly (ethylene glycols) (mPEG's) or other suitable alkyl-substituted PAO derivatives such as those containing a $C_1$–$C_4$ terminal group. Straight-chained non-antigenic polymers such as monomethyl PEG homopolymers are preferred. Alternative polyalkylene oxides such as other poly(ethylene glycol) homopolymers, polypropylene gylcols, other alkyl-poly(ethylene oxide) block copolymers, and copolymers of block copolymers of poly(alkylene oxides) are also useful. Branched PAO's such as those disclosed in commonly-assigned the PCT International Application having International Publication No. WO95/ 11924 are also of use herein. The disclosure of WO95/11924 is hereby incorporated by reference herein.

Alternative polymer substances useful herein include materials such as dextrans, polyvinyl pyrrolidones, polyacrylamides or other similar non-immunogenic polymers. Those of ordinary skill in the art will appreciate that these polymers can also be functionalized and included in the invention. The foregoing is merely illustrative and not intended to restrict the type of non-antigenic polymers suitable for use herein.

Thus, (R) is a water-soluble, substantially non-antigenic polymer residue. When the (R) is PEG or mPEG, molecular weights of between about 200 and about 100,000 daltons are preferred; molecular weights of about 1,000–50,000 daltons are more preferred and molecular weights of about 2,500–25,000 daltons are most preferred.

2. AMINE PORTION OF ACTIVATED POLYMER

In one aspect of the invention, amine-based polymer intermediates are provided. The amine portion of the intermediates can be a secondary, tertiary or quaternary amine moiety, represented herein as (B) in formula (I). Preferably, however, either secondary or tertiary amines are used.

When a secondary amine is selected for (B), amines of the formula (II) are preferred:

$$—NH(CH_2)_nX \qquad (II)$$

wherein (n) is an integer from 1–12, inclusive; and (X) is selected from the group consisting of H; OH; $CO_2R_1$, where $R_1$ is H or a $C_{1-6}$ alkyl; halogen; aryl moieties and heteroaromatic moieties.

These secondary amine moieties can be synthesized using standard organic techniques or can be readily obtained using reagents available from commercial sources. A non-limiting list of secondary amines meeting these criteria include: primary amines such as ethanolamine, beta-alanine ethyl ester, paramethoxybenzylamine, etc.

When a tertiary amine is desired for (B), amines of formulae (III–VI) are preferred:

$$\begin{array}{c} Z \\ | \\ —N(CH_2)_mX \end{array} \qquad (III)$$

$$—N\underset{\phantom{X}}{\diagup\!\!\diagdown}Y—(CH_2)_mX \qquad (IV)$$

$$—N\underset{\phantom{X}}{\diagup\!\!\diagdown}\phantom{XX} \qquad (V)$$
$$\phantom{XXXXX}(CH_2)_mX$$

$$—N\underset{\phantom{X}}{\diagup\!\!\diagdown}\phantom{XX} \qquad (VI)$$
$$\phantom{XXXXX}(CH_2)_mX$$

wherein (m) is an integer from 0–12, inclusive;

(X) is selected from the group consisting of H; OH; $CO_2R_1$, where $R_1$ is H or a $C_{1-6}$ alkyl; halogen, aryl moieties and heteroaromatic moieties;

(Y) is N or CH; and (Z) is a $C_{1-6}$ alkyl.

The tertiary amine moieties can be synthesized using standard organic techniques or can be readily obtained from commercial sources. A non-limiting list of tertiary amines meeting these criteria include secondary amines such as N-methylethanolamine, piperidine-3-methanol, N-hydroxypropylpiperazine, sarcosine ethyl ester, etc.

3. SYNTHESIS OF POLYMERS INTERMEDIATES

The polymer intermediates of formula (I) can be synthesized using conventional reaction techniques. For example, mPEG-Cl can be reacted with ethanolamine available from Aldrich or any other suitable primary amine in water and a sealed container at temperatures of approximately 60° C. to form secondary amine polymer intermediates.

Similarly, mPEG-Cl can be reacted with secondary amines such as N-methylethanolamine under similar conditions to form tertiary amine polymer intermediates.

In still other aspects of the invention, the amine-bearing groups (B) can also include an acid moiety, preferably as part of the alkyl portion thereof. A non-limiting list of suitable acids include sulfonates, carboxylates and phosphonates. As demonstrated in Examples 12–16, a trifunctional spacer moiety such as lysine or serine is first reacted with an activated polymer such as a PEG-succinimidyl succinate ester or a PEG-succinimidyl carbonate. Next, an anion group is added by modifying one of the remaining functional groups on the (B) portion of the intermediate. Reagents such as chloroethane sulfonic acid sodium salt, phosphonic acid esters or salts or ethylbromoacetate can be used. (Ethylbromoacetate first forms a carboxylate ester and then can be saponified to a salt.) Finally, the third functional group of (B) can be modified with a leaving group (L) described below in section 4.

The foregoing is merely illustrative of syntheses useful to prepare the intermediates. It is to be understood that alternative methods and reagents may be used without departing from the spirit of the invention. In essence, each (R) and (B) is joined by a reaction between nucleophilic functional groups. Each (R) is suitably functionalized, i.e. mPEG-halides such as mPEG—Cl; PEG sulfonate esters such as PEG-tosylate, etc. to undergo nucleophilic substitution and bond with (B). Functionalization of polymers with halides or sulfonate esters is readily apparent to those of ordinary skill in the art.

4. ACTIVATED AMINE-BASED POLYMERS

In yet another aspect of the invention, the intermediates described above are included as part of activated polymers which can be used to conjugate with biologically-active nucleophiles. The polymers have the formula:

R—B'—W—L    (VII)

wherein (R) is a water-soluble, substantially non-antigenic polymer residue;

(B') is NY, wherein Y is H, i.e., a secondary amine or a $C_{1-6}$ alkyl or cycloalkyl, i.e. a tertiary amine.

(W) is a spacer group; and (L) is a functional group capable of bonding with nucleophiles.

The (R—B') portion of the polymer can be prepared as described above with regard to (R—B).

The moiety (W) of Formula (VII) represents a spacer group between the (R—B') and the leaving group (L). It has been found that straight or branched lower alkyls i.e. $C_{1-4}$, aralkyl, aryl or heteroaryl groups may be employed. In this regard, alternative (W) substitutents include benzyl, substitututed benzyls, phenylethyl, substituted phenylethyls, phenyl, substituted phenyls, thiophene derivatives, pyridine derivatives, hydroxyanaline, etc. The foregoing list of (W) substitutents is to understood as being illustrative of suitable moieties and not an exclusive list. Those of ordinary skill will realize that functional equivalents of the foregoing are also possible for (W).

The spacer adjusts the geometry of the system in order to prevent undesirable side reactions, thus increasing the yield of the desired polymer-nucleophile conjugate.

Preferred spacer groups (W) include:

1. ethyl-3-isocyanato propionate; and
2. ethyl-2-aminobutyrate.

The spacer groups are available from commercial sources or can be synthesized using standard laboratory techniques.

Furthermore, the spacer groups can be attached to the (R—B) portion of the polymer by simple nucleophilic or electrophilic substitution reactions and as a result, modifying the (X) portion of the secondary or tertiary amines of Formulas (II)-(VII).

The moiety (L) of Formula (VII) represents leaving groups that "activate" the amine-based polymers of the present invention for conjugation with nucleophiles.

(L) can be a moiety selected from:

I. Functional groups capable of reacting with an amino group such as:
  a) carbonates such as the p-nitrophenyl, or succinimidyl;
  b) carbonyl imidazole;
  c) azlactones;
  d) cyclic imide thiones;
  e) isocyanates or isothiocyanates; or
  f) other active esters.

II. Functional groups capable of reacting with carboxylic acid groups and reactive carbonyl groups such as:
  a) primary amines; or
  b) hydrazine and hydrazide functional groups such as acyl
  hydrazides, carbazates, semicarbazates, thiocarbazates, etc.

III. Functional groups capable of reacting with mercapto groups such as unsaturated maleimides.

5. SYNTHESIS OF ACTIVATED AMINE-BASED POLYMERS

Figure 2:
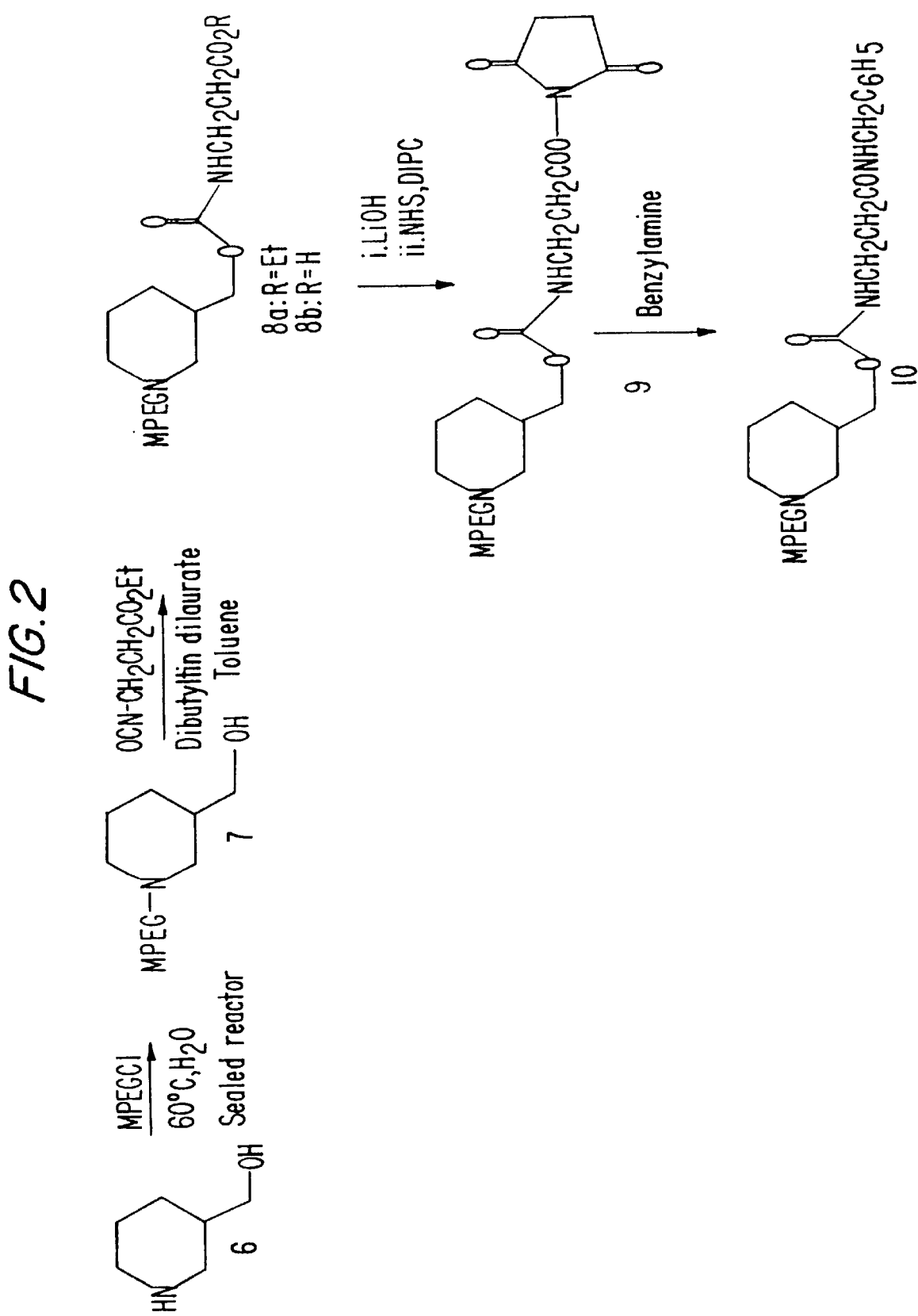
FIG. 2 is a schematic representation of synthesis techniques carried out in accordance with the invention to prepare the compounds described in Examples 2 and 7–9.
Figure 3:
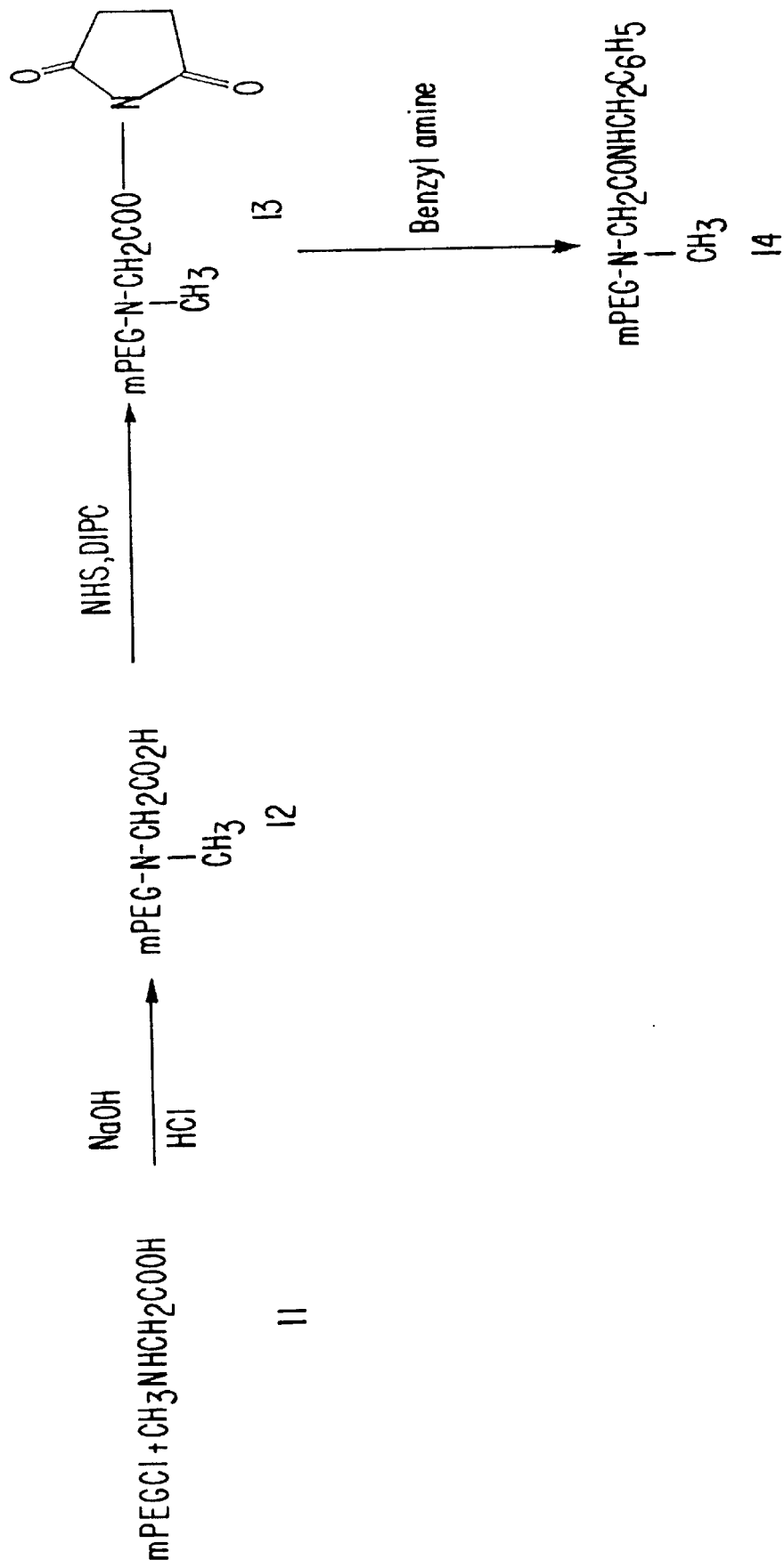
FIG. 3 is a schematic representation of the reactions carried out in Examples 10–11.
Figure 4:
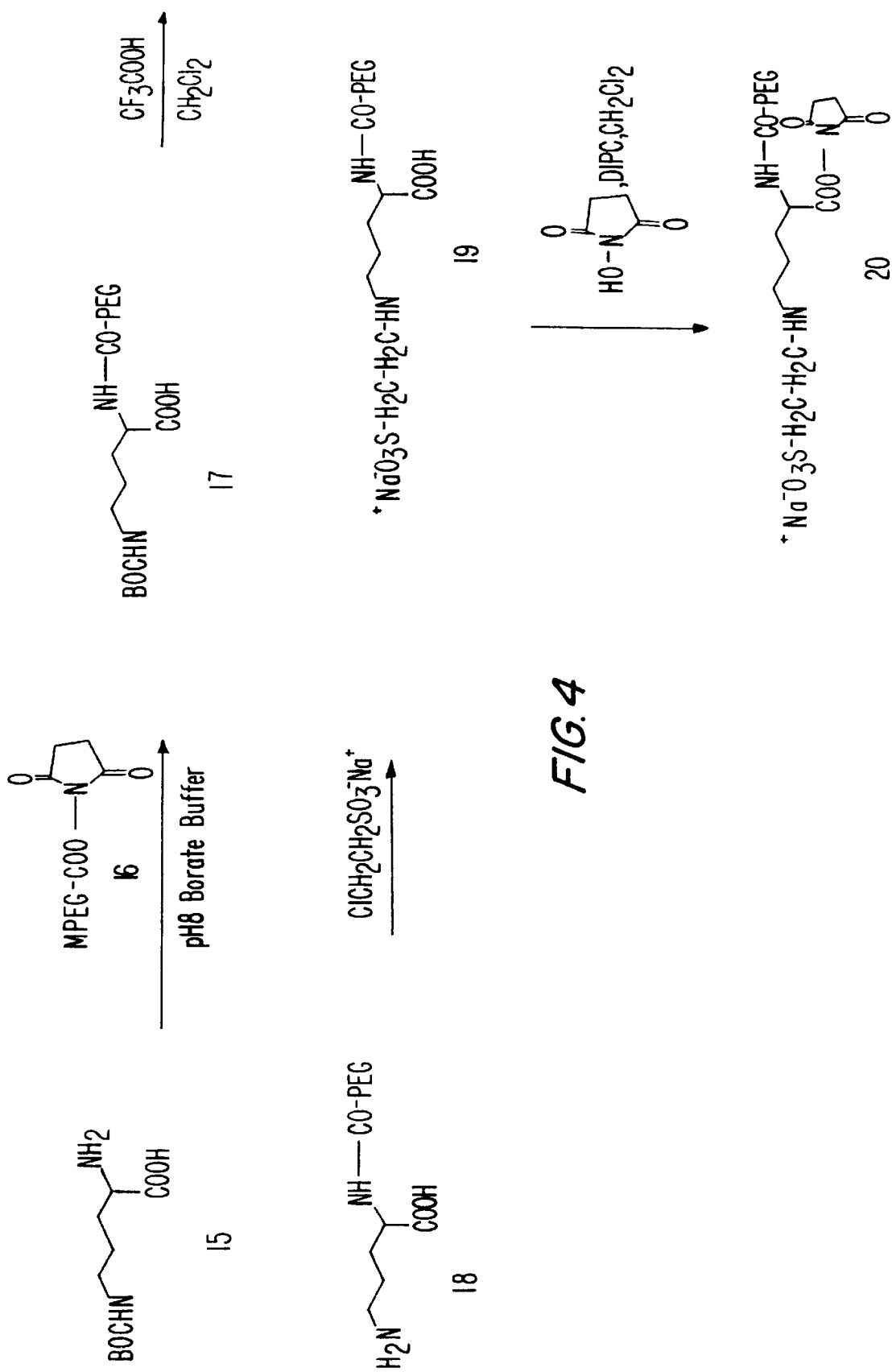
FIG. 4 is a schematic representation of the reactions carried out in Examples 12–16.

The activated polymers are formed using conventional reaction techniques. For example, an alcohol form of the intermediate (R—B), formula (I), or the intermediate (R—B'—W) of formula (VII) can be reacted with N-hydroxysuccinimide and diisopropylcarbodiimide, both available from Aldrich, in dry methylene chloride at a temperature of about 25° C. Other inert organic solvents such as toluene, THF, etc can be used and temperatures ranging from 1–100° C. can be employed. Synthesis reactions are schematically shown in FIGS. 1–4 for both secondary and tertiary amine-containing activated polymers.

6. BIOLOGICALLY ACTIVE MATERIALS SUITABLE FOR CONJUGATION

The nucleophiles conjugated with the polymers are described as "biologically active". The term, however, is not limited to physiological or pharmacological activities. For example, some nucleophile conjugates such as those containing enzymes, are able to catalyze reactions in organic solvents. Likewise, some inventive polymer conjugates containing proteins such as concanavalin A, immunoglobulin and the like are also useful as laboratory diagnostics. A key feature of all of the conjugates is that at least some portion of the activity associated with the unmodified bio-active material is maintained.

In other aspects of the invention, the conjugates are biologically active and have numerous therapeutic applications. Mammals in need of treatment which includes a biologically active material can be treated by administering an effective amount of a polymer conjugate containing the desired bioactive material. For example, mammals in need of enzyme replacement therapy or blood factors can be given polymer conjugates containing the desired material.

The therapeutically effective doses of the conjugates will be apparent to those of ordinary skill in the invention. It is contemplated, however, that the doses will be calculated of the basis of the biologically active material present in the conjugates.

Biologically active nucleophiles of interest of the present invention include, but are not limited to, proteins, peptides, polypeptides, enzymes, organic molecules of natural and synthetic origin such as medicinal chemicals and the like.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Proteins, polypeptides and peptides of interest include, but are not limited to, hemoglobin, serum proteins such as blood factors including Factors VII, VIII, and IX; immunoglobulins, cytokines such as interleukins, α-, β- and γ-interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related alleles, growth factors such as tissue growth factors, such as TGFα's or TGFβ's and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the biologically active nucleophiles of the present invention.

The biologically active nucleophiles of the present invention also include any portion of a polypeptide demonstrating in vivo bioactivity. This includes amino acid sequences, antisense moieties and the like, antibody fragments, single chain antibodies. see, for example U.S. Pat. No. 4,946,778, disclosure of which is incorporated herein by reference, binding molecules including fusions of antibodies or fragments, polyclonal antibodies, monoclonal antibodies, catalytic antibodies, nucleotides and oligonucleotides.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained form transgenic animals, i.e., mice, pigs, cows, etc., wherein the proteins expressed in milk, blood or tissues. Transgenic insects and baculovirus expression systems are also contemplated as sources. Moreover, mutant versions of proteins, such as mutant TNF's and/or mutant interferons are also within the scope of the invention.

Other proteins of interest are allergen proteins such as ragweed, Antigen E, honeybee venom, mite allergen, and the like. However, useful biologically active nucleophiles are not limited to proteins and peptides. Essentially any biologically-active compound is included within the scope of the present invention. Chemotherapeutic molecules such as pharmaceutical chemicals i.e. anti-tumor agents such as taxol, taxanes, camptothecin, anthracyclines, methotrexate, etc., cardiovascular agents, anti-neoplastics, anti-infectives, anti-anxiety agents, gastrointestinal agents, central nervous system-activating agents, analgesics, fertility or contraceptive agents, anti-inflammatory agents, steroidal agents, anti-uricemic agents, cardiovascular agents, vasodilating agents, vasoconstricting agents and the like can all be conjugated with the amine-bearing polymers of the present invention.

The foregoing is illustrative of the biologically active nucleophiles which are suitable for conjugation with the polymers of the invention. It is to be understood that those biologically active materials not specifically mentioned but having suitable nucleophilic groups are also intended and are within the scope of the present invention.

7. SYNTHESIS OF BIOLOGICALLY ACTIVE CONJUGATES

One or more of the activated polymers can be attached to a biologically active nucleophile by standard chemical reactions. The conjugate is represented by the formula:

wherein:
(R) is a water-soluble substantially non-antigenic polymer residue;
(B') is NY, wherein Y is H, i.e. a secondary amine or a $C_{1-6}$ alkyl or cycloalkyl, i.e. a tertiary amine;
(W) is a spacer moiety;
($L^1$) represents a covalent linkage between (R—B'—W) and the nucleophile; and
(z) Represents the number of polymers attached to the nucleophile.

The variable (z) is an integer $\geq 1$ representing the number of polymers conjugated to the biologically active nucleophile. The upper limit for (z) will be determined by the number of available nucleophilic attachment sites and the degree of polymer attachment sought by the artisan. The degree of conjugation can be modified by varying the reaction stoichiometry using well-known techniques. More than one polymer conjugated to the nucleophile can be obtained by reacting a stoichiometric excess of the activated polymer with the nucleophile.

The biologically active nucleophiles can be reacted with the activated polymers in an aqueous reaction medium which can be buffered, depending upon the pH requirements of the nucleophile. The optimum pH for the reaction is generally between about 6.5 and about 8.0 and preferably about 7.4 for proteinaceous/polypeptide materials. Organic/chemotherapeutic moieties can be reacted in non-aqueous systems. The optimum reaction conditions for the nucleophile's stability, reaction efficiency, etc. is within level of ordinary skill in the art. The preferred temperature range is between 4° C. and 37° C. The temperature of the reaction medium cannot exceed the temperature at which the nucleophile may denature or decompose. It is preferred that the nucleophile be reacted with an excess of the activated polymer. Following the reaction, the conjugate is recovered and purified such as by diafiltration, column chromatography, combinations thereof, or the like.

It can be readily appreciated that the activated non-antigenic polymers of the present invention are a new and useful tool in the conjugation of biologically active materials, especially when shifts in pI and/or pH optimum are sought.

EXAMPLES

The following non-limiting examples illustrate certain aspects of the invention. All parts and percentages are by weight unless otherwise noted and all temperatures are in degrees Celsius. The numbers associated with all compositions in the examples correspond to those shown in the figures.

MATERIALS

Methoxypoly(ethylene glycol) (m-PEG) having a molecular weight of about 5,000 was obtained from Union Carbide. All polyethylene glycols were molecular weight 5,000 unless stated otherwise. The solvents were obtained from Aldrich Chemical of Milwaukee, Wis. Each of the products prepared was confirmed structurally by carbon—13 NMR.

Example 1 m-PEG—Cl:

A total of 1 kg (0.2 moles) of M-PEG—OH was placed under high vacuum and heated to 70° C. with stirring until the evolution of gas ($H_2O$) ceased after approximately 4 hours. The temperature was lowered to 50° C., followed by the addition of 100 ml (1.4 moles) of thionyl chloride. This mixture was stirred overnight at 70° C. under nitrogen, cooled to 30° C., and titrated with ethyl ether to yield 990 g (99% yield) of product. $^{13}$C NMR: (CDCl$_3$)δ; $\underline{C}H_2CL$, 42.3.

Example 2 m-PEG Piperidinemethanol (7):

A mixture of 25.0 g (5.0 mmoles) of m-PEG-Cl and 5.75 g (50 mmoles) of 3-piperidinemethanol (6) in 100 ml of water was placed in a 250 ml polypropylene bottle. The bottle was sealed and kept in a water bath at 60° C. for 48 hours followed by cooling to room temperature and removal of the solvent by distillation in vacuo. Recrystallization of the residue from 2-propanol yielded of product (7). $^{13}$C NMR: (CDCl$_3$δ); $\underline{C}H_2$ (ring), 23.94, 26.47; $\underline{C}HCH_2OH$, 37.56; CH$_2$N, 53.91, 56.96, 57.38; $\underline{C}H_3O$, 57.93; $\underline{C}H_2OH$, 65.05.

Example 3

M-PEG Piperazinepropanol (2):

A mixture of 25.0 g (5.0 mmoles) of m-PEG-Cl and 7.2 g (50 mmoles) of N-hydroxypropylpiperazine (1) in 100 ml of water was placed in a 250 ml polypropylene bottle. The bottle was sealed and kept in a water bath at 60° C. for 48 hours followed by cooling to room temperature and removal of the solvent by distillation in vacuo. Recrystallization of the residue from 2-propanol yielded 24.5 g (96% yield) of product (2). $^{13}$C NMR: (CDCl$_3$)δ; $\underline{C}H_2CH_2OH$, 26.85; CH$_2$N (endocyclic), 52.19, 52.48; $\underline{C}H_2N$ (exocyclic), 56.66, 56.81; $\underline{C}H_3O$, 57.90; $\underline{C}H_2OH$, 62.18.

Example 4

Synthesis of Compound (3a)

mPEG-piperazine propanol (2), (16 g, 3.1 mmol) in toluene (240 ml) was azeotroped for 2 hours, followed by the removal of 100 ml toluene. Thereafter, ethyl-3-isocynatopropionate (1.34 g, 9.36 mmol) and dibutyl tin dilaurate (0.99 g, 1.56 mmol) were added to this solution at room temperature. The resulting mixture was heated to 60° C. for 30 hours. The solvent was removed under reduced pressure and the solid obtained was recrystallized from 2-propanol to give (3a) in 96% yield. $^{13}$C NMR: (CDCL$_3$) δ; 13.43 (OCH$_2\underline{C}H_3$); 25.40 (CH$_2\underline{C}H_2CH_2$); 33.63 ($\underline{C}H_2C$); 35.73 (CN$\underline{C}H_2$); 51.56, 52.19 ($\underline{C}H_2N$ endocyclic); 53.92, 56.61 ($\underline{C}H_2N$ exocyclic); 58.11 (OCH$_3$); 59–60 (O$\underline{C}H_2CH_3$); 62.01 ($\underline{C}H_2OC$); 155.62 (O$\underline{C}N$);171.14 ($\underline{C}OC_2H_5$).

Example 5

Synthesis Of Compound (3b)

Compound (3a) (15 g, 2.9 mmol) was dissolved in H$_2$O (200 ml) followed by the addition of lithium hydroxide (733 mg, 125 mmol). The solution was stirred for 18 hours and pH was adjusted to 4.0 using 6N HCl. The aqueous solution was extracted with methylene chloride and the solvent was removed in vacuo. The solid obtained was recrystallized from CH$_2$Cl$_2$/ether to give (3b) in 96.6% yield. $^{13}$C NMR: (CDCl$_3$) δ; 24.21 (CH$_2\underline{C}H_2CH_2$; 33.49 ($\underline{C}H_2C$); 35.94 (NH$\underline{C}H_2$); 49.71, 50.52 ($\underline{C}H_2N$ endocyclic); 53.29, 55.79 ($\underline{C}H_2N$ exocyclic); 58.12 (OCH$_3$); 61.19 ($\underline{C}H_2OC$), 155.49 (O$\underline{C}N$); 172.96 ($\underline{C}OH$).

Example 6

A. Synthesis Of Compound (4)

Compound 3b (14 g, 2.71 mmol) was dissolved in anhydrous methylene chloride (70 ml) followed by the addition of N-hydroxysuccinimide (619 mg; 5.4 mmol) and 1,3-diisopropyl carbodiimide (683 mg, 5.42 mmol). The mixture was stirred overnight at room temperature. The resulting solids were filtered and the solvent was removed under reduced pressure. The crude product was recrystallized from 2-propanol to give compound (4) in 94% yield. $^{13}$C NMR: (CDCl$_3$) δ; 24.84 (CH$_2\underline{C}H_2\underline{C}H_2$, succinimide); 30.94 ($\underline{C}H_2C$); 35.74 (N$\underline{C}H_2$); 49.84, 49.98, 50.05, 50.74 ($\underline{C}H_2N$ endocyclic); 53.29, 55.90 ($\underline{C}H_2N$ exocyclic); 58.15 (O$\underline{C}H_3$); 61.48 ($\underline{C}H_2OC$); 155.56 ($\underline{C}N$); 166.51 ($\underline{C}H_2CO$); 168.73 ($\underline{C}$ succinimide).

B. Synthesis Of Compound (5) By Conjugation Of Compound (4) With Benzylamine

Benzylamine (9 μl) was added to the solution of compound (4) (0.4 g) in CDCl$_3$ in the NMR tube. Resulting solids were dissolved by gentle heating and tapping and left at room temperature for 18 hours. $^{13}$C NMR of the resulting solution indicates the formation of product. Thus, it is shown that the amine-based polymers of the present invention react readily with nucleophiles to form conjugates. $^{13}$C NMR: (CDCl$_3$) δ; 24.67 (CH$_2\underline{C}H_2CH_2$); 24.58 (CH$_2$ free succinimide); 34.87 ($\underline{C}H_2C$); 36.50 (HN$\underline{C}H_2$); 42.31, 42.81 ($\underline{C}H_2$benzyl); 50.76, 51.18 ($\underline{C}H_2N$ endocyclic); 53.58, 56.16 ($\underline{C}H_2N$); 58.12 ($\underline{C}H_3O$); 61.50 ($\underline{C}H_2OC$); 126.77 to 138.11 ($\underline{C}$ Benzene ring); 155.67 ($\underline{C}N$); 170.77 (CH$_2\underline{C}ON$); 172.55 (CO free succinimide).

Example 7

Synthesis Of Compound (8a)

mPEG-piperidine methanol (7) (5 g, 1 mmol) in toluene (75 ml) was azeotroped for 2 hours, followed by the removal of 30 ml toluene. To this solution ethyl-3-isocyanate propionate (421 mg, 2.9 mmol) and dibutyl tin dilaurate (310 mg, 0.49 mmol) were added at room temperature were added and the resulting mixture was heated to 60° C. for 30 hours. The solvent was removed under reduced pressure and the solid obtained was recrystallized from 2-propanol to give (8a) in 91% yield. $^{13}$C NMR: (CDCl$_3$) δ; 13.30 (OCH$_2\underline{C}H_3$); 23.32

(CH$_2$ ring); 33.47 (CH$_2$C); 35.65 (NCH$_2$); 34.75 (CH$_2$ ring); 53.37, 56.32 (CH$_2$N); 57.94, (OCH$_3$); 59.42 (OCH$_2$CH$_3$); 66.17 (CH$_2$OC); 155.49 (CN); 170.92 (CH$_2$CO).

Example 8

Synthesis Of Compound (8b)

Compound (8a), (4.5 g, 0.86 mmol) was dissolved) in H$_2$O (60 ml) followed by the addition of lithium hydroxide (216 mg, 5.15 mmol). The solution was stirred for 18 hours and pH was adjusted to 4.0 using 6N HCl. The aqueous solution was extracted with CH$_2$Cl$_2$ and the solvent was removed under reduced pressure. The solid obtained was recrystallized from CH$_2$Cl$_2$/ether mixture to give (8b) in 98% yield. $^{13}$C NMR: (CDCl$_3$) δ; 21.23, 24.19 (CH$_2$ ring); 32.95 (CH$_2$C); 133.88 (CH ring); 36.12 (NCH$_2$); 57.99, (OCH$_3$); 64.90 (CH$_2$OC); 155.27 (OCN); 173.56 (C—OH).

Example 9

A. Synthesis Of Compound (9)

Compound (8b) (2 g, 0.38 mmol) was dissolved in anhydrous methylene chloride (10 ml) followed by the addition of N-hydroxysuccinimide (88.3 mg, 0.77 mmol) and 1,3diisopropylcarbodiimide (96.7 mg, 0.77 mmol). The mixture was stirred overnight at room temperature. The resulting solids were filtered and the solvent was removed under reduced pressure. The crude product was recrystallized from 2-propanol to give compound (9) in 88% yield. $^{13}$C NMR: (CDCl$_3$) δ; 21.67, 24.65 (CH$_2$ ring); 24.50 (CH$_2$ succinimide); 30.62 (CH$_2$C); 33.36 (CH ring); 35.58 (NCH$_2$); 52.64, 54.98, 55.06 (CH$_2$N); 57.94 (OCH$_3$); 155.32 (OCN); 166.31 (CH$_2$CO); 168.60 (succinimide).

B. Synthesis Of Compound (10) By Conjugation With Compound (9) With Benzylamine

Benzylamine (9.1 μl) was added to the solution of compound (9) (0.4 g) in CDCl$_3$ in the NMR tube. Resulting solids were dissolved by gentle heating and tapping and left at room temperature for 18 hours. $^{13}$C NMR of the resulting solution indicates the formation of product (10). $^{13}$C NMR: (CDCl$_3$) δ; 21.80, 21.49 (CH$_2$ ring); 24.39 (CH$_2$, succinimide); 33.44 (CH$_2$C); 36.39 (CH$_2$N); 34.72 (CH ring); 42.08, 42.65 (CH$_2$ benzylamine); 52.51, 55.07, 55.98 (CH$_2$N); 57.91 (OCH$_3$); 126.06 to 138.03 (C Benzene ring); 155.53 (OCN); 170.56 (CH$_2$CN); 172.31 (C succinimide).

Example 10

Synthesis Of N-Peg Sarcosine (12)

mPEG—Cl (25 g, 4.98 mmol) was added to the solution of N-methyl glycine (sarcosine) (11) in NaOH solution (150 ml, 0.33 M) and the mixture was placed in a sealed polypropylene bottle and heated at 75° C. for 4 days. The reaction mixture was cooled to room temperature and pH was adjusted to 6.0/6.5 with dilute HCl. The aqueous solution was extracted with CH$_2$Cl$_2$ and the solvent was removed under reduced pressure. The resulting solid was recrystallized from 2-propanol to give compound (12) in 77% yield. $^{13}$C NMR: (CDCl$_3$) δ; 41.31 (NCH$_3$); 54.57 (CH$_2$N); 57.85 (CH$_2$C); 58.04 (OCH$_3$); 167.98 (CO).

Example 11

A. Synthesis Of Compound (13)

mPEG sarcosine (12) (18 g, 3.55 mmol) was dissolved in anhydrous methylene chloride (90 ml) followed by the addition of N-hydroxysuccinimide (612 mg, 5.32 mmol) and diisopropyl carbodiimide (671 mg, 5.32 mmol). The mixture was stirred overnight at room temperature. The resulting solids were filtered and the solvent was removed in vacuo. The crude product was recrystallized from 2-propanol to give the compound (13) in 94% yield. $^{13}$C NMR: (CDCl$_3$) δ; 24.73 (CH$_2$ succinimide); 41.60 (N—CH$_3$); 54.57 (NCH$_2$); 54.44 (CH$_2$C); 58.11 (OCH$_3$); 165.13 (CO) 168.48 (C succinimide).

B. Synthesis Of Compound (14) By Conjugation With Compound (13) With Benzylamine Benzylamine (41.45 mg, 0.39 mmol) was added to Compound (13) (1 g, 0.19 mmol) in anhydrous CH,Cl, (5 ml). The reaction mixture was kept at room temperature overnight. The solvent was removed under reduced pressure and the residue was recrystallized from 2-propanol to give compound (14) in 80% yield. $^{13}$C NMR: (CDCl$_3$) δ; 41.94 (NCH$_3$); 42.65 (CH$_2$ Benzylamine); 56.32 (NCH$_2$); 58.12 (OCH$_3$); 60.22 (CH$_2$C); 126.32 to 137.99 (C Benzene ring);169.70 (CO).

Example 12

N-epsilon-Boc lysine (15), (0.246 g, 1 mmol) PEG 5,000-N-hydroxysuccinimide ester (16) (5 g, 1 mmol) are added to pH 8 borate buffer (30 ml). The mixture is stirred at room temperature for about 3 hours and then neutralized with dilute hydrochloric acid. The aqueous solution was extracted with dichloromethane (3×20 ml). The organic layer was dried (anhyd. Na$_2$SO$_4$) and evaporated under reduced pressure to yield 4.1 g, 79% N-epsilon-tert.-butoxycarbonyl-alpha PEGcarbamate of L-lysine (17)

Example 13

N-epsilon-tert.-butoxycarbonyl-alpha PEGcarbamate of L-lysine (17) (5.2 g; 1.0 mmol) is dissolved in trifluoroacetic acid and dichloromethane (1:2, 30 ml) and left to stand at room temperature for one hour. The solution is evaporated to dryness in vacuo and the residue is triturated with dry ether, filtered, washed with ether and dried in vacuo to yield (3 g, 60%) of lysine-N-alpha-PEGcarbamate (18).

Example 14

A mixture of lysine-N-alpha-PEGcarbamate (18) (5.1 g, 1 mmol) chloroethane sulfonic acid sodium salt (1.84 g, 10 mmol) in 20 ml of water is placed in a 10 ml polypropylene bottle. The bottle is sealed and kept in a water bath at 60° C. for 48 hours followed by cooling to room temperature and removal of the solvent by distillation in vacuo. Recrystallization of the residue from 2-propanol yields (5.5 g, 80%) of the compound (19).

Example 15

A solution of the compound (19) (5.2 g, 1 mmol) and N-hydroxysuccinimide (115 mg, 1 mmol) in dry dichloromethane is cooled in an ice water bath and diisopropylcarbodiimide (0.126 g. 1 mmol) is added with stirring. The mixture is kept in a refrigerator overnight. The solvent is removed and the solid obtained is recrystallized from 2-propanol to give 4.3 g, (80%) of the product (19).

Example 16

The following procedure details the conjugation of bovine hemoglobin (Hb), 9.8% solution, using an 18 fold molar excess of piperidine pI PEG (9) in the presence of 10% NaCl.

Piperidine pI PEG (9) 1.461 g, 2.842×10$^{-4}$M, is dissolved in 2 ml of pH 7.0 phosphate buffer (0.1M) in a jacketed reaction vessel (0° C.) and stirred for 10 minutes. Ten ml of the Hb solution is pipetted into another jacketed reaction vessel (8° C.), along with 2.3 g NaCl. The pH is adjusted to 7.8. The pI PEG solution is added to the reaction vessel containing the Hb and the container is washed with 2×0.5 ml of the pH 7.0 buffer. The washings are then transferred to the Hb vessel. Seven ml of pH 7.8 phosphate buffer is added and the pH is adjusted to 7.8 with 1.0N NaOH. The reaction mixture is stirred uniformly and slowly for about 2 hours at 8° C. while maintaining the pH at 7.8.

After 2 hours, the reaction is quenched with cysteine HCl (0.105 g) and 124 μl of glycine solution (2.25×10$^{-4}$M). The pH is adjusted to 7.8 with 2N NaOH. The conjugate can now be stored in the refrigerator between 4–6° C.

As will be readily appreciated, numerous variations and combinations of the features set forth above can be utilized without departing from the present invention as set forth in the claims. Such variations are not to be regarded as a departure from the spirit and scope of the invention, and all such modifications are intended to be included within the scope of the following claims.

What is claimed is:

1. A polymer conjugate comprising the formula:

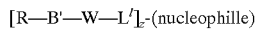

[R—B'—W—L$^1$]$_z$-(nucleophille)

wherein:
- (R) is a water soluble substantially non-antigenic polymer residue;
- (B') is a secondary or tertiary amine,
  - when B' is a tertiary amine, (W) is a spacer moiety selected from the group consisting of straight or branched $C_{1-4}$ alkyls, aralkyl, aryl, heteroaryl moieties, C(O)NHCH$_2$CH$_2$C(O) and CH$_2$(O);
  - when B' is a secondary amine, (W) is selected from the group consisting of aralkyl, aryl, heteroaryl moieties, C(O)NHCH$_2$CH$_2$C(O) and CH$_2$C(O);
- (nucleophile) is a member of the group consisting of proteins and chemotherapeutic agents;
- (L$^1$) represents a covalent linkage between (R—B'—W) and the nucleophile; and
- (z) represents the number of polymers attached to the nucleophile.

2. The conjugate of claim 1, wherein R is a poly(alkylene oxide).

3. The conjugate of claim 2, wherein said poly(alkylene oxide residue is capped with a $C_{1-4}$ alkyl group distal to said covalent linkage (L$^1$).

4. The conjugate of claim 3, wherein said poly(alkylene oxide) is selected from the group consisting of poly(ethylene glycol) homopolymers, alkyl-capped poly(ethylene oxides), and copolymers of block copolymers of poly(alkylene oxides).

5. The conjugate of claim 1, wherein said poly(alkylene oxide) has a molecular weight between about 200 and about 100,000 Daltons.

6. The conjugate of claim 5, wherein said poly(alkylene oxide) has a molecular weight between 1,000 and about 50,000 Daltons.

7. The conjugate of claim 6, wherein said poly(ethylene glycol) homopolymer has a molecular weight of about 2,500 and about 25,000 Daltons.

8. The conjugate of claim 1, wherein R is a poly(ethylene glycol) homopolymer.

9. The conjugate of claim 1, where in said nucleophile is a protein.

10. The conjugate of claim 9, wherein said protein is selected from the group consisting of polyclonal antibodies, monoclonal antibodies, fragments of antibodies and single chain antibodies.

11. The conjugate of claim 1, wherein said nucleophile is a peptide.

12. The conjugate of claim 1, wherein said nucleophile is an enzyme.

13. The conjugate of claim 1, wherein said nucleophile is a polypeptide.

14. The conjugate of claim 12, wherein said enzyme is glucocerebrosidase.

* * * * *